United States Patent [19]
Hennessey

[11] Patent Number: 5,278,172
[45] Date of Patent: Jan. 11, 1994

[54] METHOD AND COMPOSITION FOR TREATING TENDON OR JOINT INFLAMMATION USING A VASODILATOR

[76] Inventor: Richard K. Hennessey, 803 Cottonwood Dr., Severna Park, Md. 21146

[21] Appl. No.: 917,891

[22] Filed: Jul. 24, 1992

[51] Int. Cl.⁵ ............................................. A61K 31/47
[52] U.S. Cl. ..................................... 514/307; 514/947
[58] Field of Search ......................... 514/307, 936, 947

[56] References Cited

U.S. PATENT DOCUMENTS

| | | | |
|---|---|---|---|
| 4,018,927 | 4/1977 | Voorhees | 424/260 |
| 4,440,777 | 4/1984 | Zupan | 424/274 |
| 4,758,433 | 7/1988 | Johnson et al. | 424/195.1 |
| 5,059,603 | 10/1991 | Rubin | 514/264 |

OTHER PUBLICATIONS

Batterman et al., Angiology 21(9), 1970, pp. 612–626.
Batterman et al., CA 74(1):2610a (Chemical Abstracts), 1970.
Matveikov et al., 89:185149 Biosis, BA87:96415, 1988.

*Primary Examiner*—S. J. Friedman
*Assistant Examiner*—William Jarvis
*Attorney, Agent, or Firm*—Foley & Lardner

[57] ABSTRACT

A process is provided which is useful in alleviating inflammation of tendons and/or joints in a patient in need of such treatment. The process comprises administering a vasodilator to the inflamed tissue, either topically or by injection. Advantageously, the vasodilator is papaverine or a pharmaceutically acceptable salt thereof such as papaverine hydrochloride. Advantageously, the papaverine hydrochloride may be administered topically in a composition comprising a carrier. The carrier dissolves the papaverine hydrochloride and enables it to penetrate the skin and be absorbed into the inflamed tissue.

11 Claims, No Drawings

METHOD AND COMPOSITION FOR TREATING TENDON OR JOINT INFLAMMATION USING A VASODILATOR

FIELD OF THE INVENTION

This invention relates to methods of treating inflammation of tendons and/or movable joints of a patient in need of such treatment. More specifically, this invention relates to a method of treating inflammation of such tissue, comprising administering a vasodilator to the subcutaneous tissue such that it contacts the tendon and/or joint. This invention also relates to methods of treating inflammation of such tissue by administering a composition comprising papaverine or a pharmaceutically acceptable salt thereof to the affected tissue.

BACKGROUND OF THE INVENTION

Inflammation of tendons and joints is characteristic of many common ailments such as osteoarthritis, rheumatoid arthritis, carpal tunnel syndrome, and tendinitis. The symptoms are often painful and debilitating. There are many currently-accepted treatments for these ailments, including prescription and non-prescription non-steroidal antiinflammatory drugs (NSAIDs), oral and injectable steroid compositions, chemotherapeutics such as methotrexate, and injectable gold solutions, to name only a few. While such treatments often can reduce the inflammation accompanying the ailment, they typically also provoke unpleasant or unacceptable side-effects.

Additionally, there are several marketed over-the-counter topical rubs which are capable of making the area lo of the skin or muscle feel hot or cold. Those rubs, however, while generally harmless in terms of unwanted side-effects, can provide only temporary topical relief and cannot relieve the inflammation which is the source of the patient's discomfort. Thus, there remains a great need for alternative methods of treating such disorders.

SUMMARY OF THE INVENTION

Accordingly, it is an object of this invention to provide a method for the treatment of inflammation of tendons and/or movable joints.

It is a further object of this invention to provide a method for the treatment of such inflammation by the topical administration of a composition to the skin surrounding the inflamed tissue.

It is a further object to provide compositions for use in treating such inflammation.

It is yet a further object to provide topically-applied compositions for use in treating such inflammation.

In accordance with one aspect of this invention, there is provided a process for treating inflammation of tendons and/or movable joints of a patient in need of such treatment comprising administering an effective amount of a vasodilator or salt thereof to the tissues of the tendon or joint.

In accordance with another aspect of this invention, there is provided a process for treating such inflammation comprising the topical administration of an effective amount of a composition comprising a therapeutically effective amount of a vasodilator or salt thereof in a pharmaceutically acceptable carrier which dissolves the vasodilator and enables the vasodilator to penetrate the skin and be absorbed into the tissues of the tendon or joint.

There also are provided compositions for carrying out the foregoing processes.

In a preferred embodiment of the process and composition of this invention, the vasodilator comprises papaverine or a pharmaceutically acceptable salt thereof such as papaverine hydrochloride.

In another preferred embodiment, the papaverine or salt thereof is in a composition with a pharmaceutically acceptable carrier which dissolves the papaverine and enables the papaverine to penetrate the skin and be absorbed into the tissues of the tendon or joint.

Additional objects and advantages of the invention will be set forth in part in the description that follows, and in part will be obvious from the description, or may be learned by practice of the invention. The objects and advantages may be realized and obtained by means of the processes and compositions particularly pointed out in the appended claims.

DETAILED DESCRIPTION OF THE PREFERRED EMBODIMENTS

It has been discovered that administering a vasodilator or pharmaceutically acceptable salt thereof to the inflamed tissue of a tendon and/or movable joint can reduce the inflammation of that tissue. Such inflammation commonly can be associated with disorders such as osteoarthritis, rheumatoid arthritis, carpal tunnel syndrome, and tendinitis. Further, it has been discovered that, to be effective, the vasodilator or salt thereof either must be capable of penetrating the skin to reach the inflamed tendon and/or joint, or it must be dissolved in a carrier which enables the vasodilator to be absorbed through the skin and into the tissues of the inflamed tendon and/or joint. Alternatively, the vasodilator, with or without a pharmaceutically acceptable carrier, can be delivered directly to the inflamed tissue or surrounding area through injection (intradermally or subcutaneously), or by surgical means.

Vasodilators which can be used in accordance with this invention include, for example, ethaverine and salts thereof, totazoline and salts thereof, nylidin and salts thereof, diazaxide, minoxidil and papaverine, which is readily available in the hydrochloride form. The foregoing are only exemplary and many other vasodilators useful in this invention will be readily apparent to those skilled in the art.

To be effective, the vasodilator must reach the inflamed tissues. Thus, where topical administration is employed, the vasodilator must be able to penetrate the skin and be absorbed into the inflamed tissues. In cases where the vasodilator itself is incapable of such penetration and absorption, a topical-use carrier that both dissolves the vasodilator and facilitates its penetration through the skin and absorption into the subcutaneous tissues is required.

Suitable topical compositions thus include those pharmaceutical forms in which the compound is applied externally by direct contact with the skin surface surround or adjacent the inflamed tissue. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., containing polyethylene glycols, as well as mixtures thereof. Preferably, the vasodilator will be completely solubilized in the composition so that it will be completely absorbed into the subcutaneous tissue.

The quantity of vasodilator administered can depend upon several factors including, inter alia, (1) the particular vasodilator used, e.g., its ability to penetrate the skin and absorb into the subcutaneous tissue, and the nature and magnitude of its effect on the tissue, (2) the method of administration, e.g., topical versus injection, (3) the carrier, and the solubility of the vasodilator in the carrier, (4) the individual requirements of the patient, and (5) possible side effects of the vasodilator. Those skilled in the art will be able to determine through the exercise of routine skill the amount of vasodilator to administer. It is contemplated that concentrations of vasodilator in topical compositions will range from less than one percent to a few percent (e.g., from about two to about four percent), to higher concentrations of five, ten, twenty or more percent by weight, especially when injectable compositions are used. Indeed, those skilled in the art may recognize vasodilators which can be administered topically or by injection without carriers, i.e., at full strength.

The topical composition so produced can be administered by massaging the composition into the external area near the inflamed tendon or movable joint. The application is then repeated as necessary, up to several times per day, depending upon the concentration of vasodilator used and the other factor described above.

In a particularly preferred embodiment of this invention, the vasodilator comprises papaverine. Papaverine is a known alkaloid of chemical formula $C_{20}H_{21}NO_4$. It is readily available in hydrochloride form from Sidmak Laboratories of East Hanover, N.J. Taken orally, papaverine hydrochloride has proven useful in the treatment of migraine headaches. When applied topically, it also is useful for treating proliferating skin diseases (see, e.g., U.S. Pat. No. 4,098,127 to Voorhees). It has been used to improve the effectiveness of vein grafting procedures, and recent research suggests that it may be useful as an anti-retroviral agent. Although the preferred embodiment comprises the hydrochloride salt of papaverine, other salts or active forms of papaverine are contemplated and will be readily apparent to those skilled in the art.

In the case of papaverine hydrochloride, acceptable results are obtained with compositions comprising up to about 5% or more by weight of papaverine hydrochloride. Using the preferred carrier described below, D-071, particularly advantageous results have been obtained with compositions comprising from about 0.5% to about 2.0% by weight of papaverine hydrochloride. It has been found that the solubility and stability of papaverine hydrochloride can be a limiting factor in terms of the practical maximum weight percent of the papaverine hydrochloride in a topical composition. That is, the solubility of a stable formulation of papaverine hydrochloride in an aqueous-based carrier has been empirically determined to be about two percent. While higher percentages, e.g., up to about five percent, are possible, it has been found that the papaverine hydrochloride will begin to crystallize out of solution over time when higher concentrations are used. Thus, better stability is achieved with aqueous-based formulations when amounts of from about 0.5% to about 2.0% by weight of papaverine hydrochloride are used. Of course, those skilled in the art may recognize other types of topical formulations or processes for formulation which will enable relatively stable compositions having higher weight percentages of papaverine hydrochloride, and such compositions are clearly contemplated in this invention.

In one advantageous embodiment, a topical use carrier can comprise FORMULA D-071, which is manufactured by Clay Park Labs, Inc., of Brooklyn, New York. According to the manufacturer, FORMULA D-071 comprises:

| Glucono delta lactone | 0.01 to 0.5% |
|---|---|
| Methylparaben | 0.1 to 0.5% |
| Hydroxyethyl cellulose | 1.0 to 5.0% |
| Glycerine, anhydrous | 7.5 to 25.0% |
| Sodium hydroxide | 0.01 to .5% |
| Chlorhexidine Gluconate | 0.025 to .75% |
| Purified water | balance |

It has been found that FORMULA D-071 will readily dissolve up to about 5% by weight of papaverine hydrochloride, although it has been found that the most stable concentrations comprise up to about 2% by weight papaverine hydrochloride. Preferably, FORMULA D-071 is purchased from Clay Park Labs. Alternatively, it can be substantially duplicated by thoroughly mixing the above-recited components and allowing the mixture to stand for about 24 hours. If any solids remain in suspension after 24 hours, the mixture may be heated in a water bath to 55° C and then allowed to cool to room temperature. The papaverine hydrochloride is then added to the FORMULA D-071, thoroughly mixed, and then allowed to sit for about 48 hours. If the papaverine hydrochloride is not completely dissolved, the mixture may be heated in a water bath to a maximum of about 55° C until a clear gel results. Of course, some routine experimentation may be required to substantially duplicate the consistency of commercially-obtained FORMULA D-071.

The topical composition so produced is administered by massaging 1 to 2 ml of gel into the external area near the inflamed tendon or movable joint. The application is repeated as necessary, up to 1, 2, 3, 4, 5, 6 or more times a day.

While not wishing to be bound by any particular theory, it is believed that the vasodilator effects the relaxation of the smooth muscles of both the arterial and venous blood vessels, which allows the vessels to dilate and increase the flow of blood through the inflamed tissues. The observed absence of edema after treatment with papaverine hydrochloride and the adsorption of serous fluids attest to the increase in venous blood flow. Since the body's immune system is carried by the blood, additional flow also increases the immune cells passing through the diseased tissues. Also, any refuse from cell action is removed through the venous system. This constant flow of pure blood through the area also could explain why the cells are not trapped, nor given the opportunity to act destructively on the healthy tissue's cells, i.e., an autoimmune action. Moreover, in the case of papaverine hydrochloride, it is believed that the observed efficacy in reducing inflammation results from complete penetration through the skin layers into the subcutaneous tissues, muscles and tendons of the movable joint, synovial membranes and possibly the cartilage.

The following examples are intended solely to illustrate the invention, and do not limit the invention in any way.

EXAMPLE 1

A composition hereinafter referred to as R-H Gel was prepared using papaverine hydrochloride and a suitable carrier. The carrier was Formula D-071, which was obtained from Clay Park Labs, Inc., of Brooklyn, N.Y. Alternatively, the carrier may be manufactured by thoroughly mixing the ingredients and heating in a water bath at 70° C. while stirring continuously until the ingredients dissolve.

Two grams of papaverine hydrochloride were thoroughly mixed with 98 g. of Formula D-071 and the resulting mixture was allowed to stand for 24 hours. The mixture was then mixed again and allowed to stand for another 24 hours, resulting in a clear gel containing about 2% by weight of papaverine hydrochloride.

EXAMPLE 2

In 1984, an orthopedic surgeon diagnosed a patient as having a serious case of osteoarthritis. To relieve the pain sufficiently for the patient to sleep, 1000 mg of Tylenol was required. The surgeon diagnosed the disease as a degenerative-type disease which only could worsen and eventually require surgery. In 1990, with no improvement in the patient's condition, the patient began to topically treat the left hip with a composition similar to that described above in Example 1. The patient applied approximately 3 ml to the front and rear of the Coxa (hip joint) four times daily until the pain and stiffness was relieved thirty days later. The patient then continued the same treatment for another thirty days. After the second thirty day period of treatment, there was a noticeable improvement in the hip joint. In September 1991, a hip X-ray showed little deterioration, when compared to the previous X-ray from 1984. The patient's hips currently are without pain.

EXAMPLE 3

The same patient as in Example 2 was diagnosed as having post-polio syndrome from having contracted the disease during his teenage years. The resulting weakness of his left side promoted osteoarthritis, rheumatoid arthritis and carpal tunnel syndrome in the joints of his left arm and leg. As in Example 2, the patient topically applied a composition comprising papaverine hydrochloride to the affected areas. All of the affected joints are now symptom free.

EXAMPLE 4

A female patient suffered from arthritis such that both joints on her right thumb were swollen and misshapen. The joints on her left thumb and the middle finger of her right hand also were swollen. Further, the tip joint of her middle finger sometimes would jump out of the socket. She applied a composition similar to that described in Example 1 to her hands every night before bed.

Presently, there is less swelling on her right thumb, which is returning to its original shape. There is neither swelling nor socket trouble on the middle finger of her right hand, nor is there swelling on her left thumb. Her fingers are limber and her rings fit as they did before the onset of arthritis.

EXAMPLE 5 from swelling on the
Another female patient suffered arch of her left foot. The condition was first diagnosed as gout, but X-rays later suggested arthritis. Treatment with two different, prescription NSAIDs proved ineffective. Stiffness and pain developed in the right thumb, which was diagnosed as osteoarthritis. The patient began treating both her thumb and left foot with a composition similar to that described in Example 1. After two weeks of treatment, swelling in the foot was relieved and the pain and stiffness in the thumb was noticeably improved. She no longer takes the NSAIDs and only occasionally uses a topical papaverine hydrochloride composition when symptoms recur.

EXAMPLE 6

A third female patient had been treating very swollen and painful index and ring fingers with NSAIDs for several weeks, with no improvement. Topically applying a papaverine gel similar to that described in Example 1 three times a day for five days eliminated all pain and swelling.

It will be apparent to those skilled in the art that various modifications and variations can be made to the compositions of matter and processes of this invention. Thus, it is intended that the present invention cover the modifications and variations of this invention provided they come within the scope of the appended claims and their equivalents. All references in the claims to a composition of matter such as a vasodilator or papaverine, whether in general or by name, expressly includes the salts and hydrates thereof.

What is claimed is:

1. A process for treating inflammation of a tendon and/or joint of a patient in need of such treatment, comprising topically administering, to an external area near to the tendon and/or joint, an effective amount of a composition comprising:
   (a) a therapeutically effective amount of an active ingredient comprising papaverine or a pharmaceutically acceptable salt thereof; and
   (b) an aqueous-based carrier for the topical administration of said active ingredient, wherein said carrier comprises at least one of glycerine or hydroxyethyl cellulose, wherein said active ingredient is at least partially soluble in said carrier, and said carrier enables the penetration of the active ingredient through the skin and absorption of said active ingredient into the subcutaneous tissue such that said active ingredient contacts the tendon and/or joint.

2. A process according to claim 1, wherein said active ingredient comprises papaverine hydrochloride.

3. A process according to claim 2, wherein said composition comprises up to about 5% by weight of papaverine hydrochloride.

4. A process according to claim 2, wherein said composition comprises from about 0.5% to about 2.0% by weight of papaverine hydrochloride.

5. A process according to claim 1, wherein said carrier predominantly comprises water.

6. A process according to claim 5, wherein said carrier comprises glycerine.

7. A process according to claim 4, wherein said carrier predominantly comprises water.

8. A process according to claim 7, wherein said carrier comprises glycerine.

9. A process according to claim 1, wherein the carrier comprises:

| | |
|---|---|
| Glucono delta lactone | 0.01 to 0.5% |
| Methylparaben | 0.1 to 0.5% |
| Hydroxyethyl cellulose | 1.0 to 5.0% |
| Glycerine, anhydrous | 7.5 to 25.0% |
| Sodium hydroxide | 0.01 to .5% |
| Chlorhexidine Gluconate | 0.025 to .75% |
| Purified water | balance |

10. A process for treating inflammation of a tendon and/or joint of a patient in need of such treatment, comprising topically administering to an external area near to said tendon and/or joint, an effective amount of a composition comprising a therapeutically effective amount of an active ingredient comprising a vasodilator or a pharmaceutically acceptable salt thereof and an aqueous-based carrier comprising glycerine or hydroxyethyl cellulose for the topical administration of said active ingredient.

11. A process according to claim 10, wherein said composition comprises a carrier for the topical administration of said active ingredient, wherein
said active ingredient is at least partially soluble in said carrier, and said carrier enables the penetration of said active ingredient through the skin and absorption of said active ingredient into the subcutaneous tissue such that said active ingredient contacts the tendon and/or joint.

* * * * *